US006432386B1

(12) United States Patent
Rollat-Corvol et al.

(10) Patent No.: US 6,432,386 B1
(45) Date of Patent: Aug. 13, 2002

(54) COSMETIC COMPOSITIONS COMPRISING AT LEAST ONE POLYMER WITH SPECIFIC CHARACTERISTICS AND AT LEAST ONE THICKENING POLYMER

(75) Inventors: Isabelle Rollat-Corvol, Paris; Pascale Cothias, Le Bretonneux, both of (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/714,208

(22) Filed: Nov. 17, 2000

(30) Foreign Application Priority Data

Nov. 19, 1999 (FR) ............................................. 99 14589

(51) Int. Cl.⁷ .............................. A61K 7/06; A61K 7/11; A61K 31/78; A61K 31/74; A61K 7/00
(52) U.S. Cl. ........................... 424/45; 424/47; 424/484; 424/70.16; 424/78.03; 424/401; 424/DIG. 2; 514/772.3; 514/944
(58) Field of Search ........................... 424/45, 70.16, 424/78.03, 484, 47, DIG. 1, DIG. 2; 514/772.3, 944

(56) References Cited

U.S. PATENT DOCUMENTS 5,753,215 A 5/1998 Mougin et al.
5,817,304 A * 10/1998 Mondet et al. .......... 424/78.03

FOREIGN PATENT DOCUMENTS

| EP | 0 628 304 | 12/1994 |
|---|---|---|
| FR | 2 108 635 | 5/1972 |
| FR | 2 730 162 | 8/1996 |
| FR | 2 750 601 | 1/1998 |
| GB | 1 530 517 | 11/1978 |

OTHER PUBLICATIONS

"Avalure™ Film Forming Polymers for Personal Care Applications", Polymers for Personal Care, BF Goodrich, TDS–248, Apr. 28, 1997, pp.1–4.
Copending Application by Isabelle Rollat–Corvol and Henri Samain, entitled Cosmetic Compositions Comprising At Least One Film–forming Polymer, filed Nov. 17, 2000.
English language Derwent Abstract for FR 2 108 635.
English language Derwent Abstract for FR 2 730 162.
English language Derwent Abstract for FR 2 750 601.

* cited by examiner

*Primary Examiner*—Frederick Krass
*Assistant Examiner*—Clinton Ostrup
(74) *Attorney, Agent, or Firm*—Finnegan, Henderson, Farabow, Garrett & Dunner, L.L.P.

(57) ABSTRACT

Cosmetic compositions comprising, in a cosmetically acceptable medium:

(1) at least one film-forming polymer (A), wherein a film obtained by drying a mixture of said polymer (A) with ethanol or water, at room temperature and at a relative humidity of 50%, has a mechanical profile defined by at least:
  (i) a degree of elongation at break ($\epsilon_r$) of greater than or equal to 300%;
  (ii) a recovery at 300 seconds ($R_{300}$) of greater than or equal to 45%; and
  (iii) if the recovery at 300 seconds ($R_{300}$) is from 45% to 60%, then the elongation at break is less than or equal to 1300%; and
(2) at least one crosslinked thickening polymer (B) comprising at least one (meth)acrylic acid monomeric, wherein said at least one polymer (B) is present in the composition in an amount ranging from at least 0.6% by weight, relative to the total weight of the composition.

20 Claims, No Drawings

COSMETIC COMPOSITIONS COMPRISING AT LEAST ONE POLYMER WITH SPECIFIC CHARACTERISTICS AND AT LEAST ONE THICKENING POLYMER

The present invention relates to cosmetic compositions comprising, in a cosmetically acceptable medium, at least one film-forming polymer (A) with specific characteristics and at least one crosslinked thickening polymer (B) comprising at least one (meth)acrylic acid monomeric residue. The invention also relates to a process for shaping or holding the hair using such compositions. Additionally, the invention relates to a process for formulating hairstyling products, in particular gels, comprising such compositions in order to hold or shape the hairstyle.

The compositions in accordance with the invention can be applied to the skin and the lips, and keratinous materials such as the hair, the eyebrows, the nails, and the eyelashes.

For the purposes of the present invention, the expression "styling composition" means any composition intended to fix and/or hold the shape of the hairstyle.

Hair products for fixing the hair that are most widely available in the cosmetics market comprise a solution, usually an alcoholic or aqueous-alcoholic solution, and a film-forming polymer that is soluble in water or in alcohol, and various cosmetic adjuvants.

However, some of these hair formulations, such as mousses, gels and especially sprays and aerosol lacquers intended to hold the shape of the hairstyle, may not always allow the hairstyle satisfactory resistance to the various natural movements in life, such as walking, head movements, or gusts of wind.

Some of the polymers used to formulate these hair products are anionic, cationic, amphoteric and nonionic film-forming polymers. These polymers may lead to the formation of films that may be of a hard and/or brittle nature.

When the polymer is too brittle, the percentage of elongation at break measured on the film is low, i.e., in general less than 2%, and the hold of the hairstyle over time may not be ensured.

To overcome at least this problem, these polymers have already been mixed with plasticizers to obtain more flexible coatings that tend not to be crumbly. However, these films are may be deformable and plastic, i.e., they may recover very little of their initial form after deformation. Although the hairstyle is improved, it may be less satisfactory because the shape of the hairstyle may change over time.

It has moreover already been proposed to combine several of these polymers. In this case, the shape of the hairstyle can last longer, but the compositions prepared may adversely affect the cosmetic properties of the hair when they are applied. For example, the hair may become coarse to the touch and may be difficult to disentangle.

Thus, it would be advantageous to find cosmetic compositions, in particular for holding and/or fixing keratin fibers, such as hair, that overcome at least one of the drawbacks mentioned above. Such cosmetic compositions would advantageously provide long-lasting fixing, while simultaneously exhibiting good cosmetic properties, such as good disentangling, softness, and a pleasant appearance.

The inventors have discovered, surprisingly and unexpectedly, that it is possible to overcome at least one of the technical problems mentioned above by using certain specific combinations of polymers in such cosmetic compositions.

One subject of the invention is a cosmetic composition comprising, in a cosmetically acceptable medium:

(1) at least one film-forming polymer (A), wherein a film obtained by drying a mixture of said polymer (A) with ethanol or water, at room temperature and at a relative humidity of 50%, has a mechanical profile defined by at least:
  (i) a degree of elongation at break ($\epsilon_r$) of greater than or equal to 300%;
  (ii) a recovery at 300 seconds ($R_{300}$) of greater than or equal to 45%; and
  (iii) if the recovery at 300 seconds ($R_{300}$) is from 45% to 60%, then the elongation at break is less than or equal to 1300%; and
(2) at least one crosslinked thickening polymer (B) comprising at least one (meth)acrylic acid monomeric residue, wherein said at least one polymer (B) is present in the composition in an amount ranging from at least 0.6% by weight, relative to the total weight of the composition.

One particular embodiment of the invention relates to an aerosol device comprising a container comprising the composition.

Another subject of the present invention relates to a process for shaping or holding the hairstyle, comprising the use of this composition.

Yet another subject of the present invention relates to the use of this composition for the manufacture of cosmetic haircare compositions, in order to hold or shape the hairstyle.

The at least one polymer (A) that is particularly targeted by the present invention is distributed by Goodrich under the names Avalure AC 315® and Hystretch V29®.

For the purposes of the present invention, the expression "film obtained by drying at room temperature and at a relative humidity of 50%" means the film obtained at 22±2° C. and at a relative humidity of 50%±5%, wherein the film is obtained under these conditions using a mixture containing 6% active material (a.m.) of the at least one polymer (A) with ethanol or water, the amount of mixture being adapted to obtain, in a Teflon matrix, a film 500±50 $\mu$m thick. The drying is continued until the weight of the film no longer changes, approximately 12 days. The at least one polymer (A) is tested in ethanol, if it is soluble or partially soluble in ethanol. If the at least one polymer (A) is not soluble or partially soluble in ethanol, then the at least one polymer (A) is tested in water in soluble or dispersed form.

For the purposes of the present invention, the degree of elongation at break and the degree of recovery are evaluated with the tests described below.

To carry out the tensile tests, the film is cut into rectangular samples 80 mm and 15 mm wide.

The tests are carried out on a machine, sold under the name Lloyd or sold under the name Zwick, under the same temperature and humidity conditions as for the drying, i.e., a temperature of 22±2° C. and a relative humidity of 50±5%.

The samples are drawn at a speed of 20 mm/min and the distance between the jaws is 50±1 mm.

To determine the instantaneous recovery ($R_i$), the following procedure is carried out:
  the sample is drawn 150% ($\epsilon_{max}$), i.e., to 1.5 times its initial length ($I_0$)
  the stress is removed by imposing a return speed equal to the tensile speed, i.e., 20 mm/min and the elongation of the sample is measured as a percentage, after return to zero load ($\epsilon_i$).

The instantaneous recovery in % ($R_i$) is given by the formula below:

$$R_i = ((\epsilon_{max} - \epsilon_i)/\epsilon_{max}) \times 100$$

To determine the recovery at 300 seconds, the sample which has undergone the above operations is maintained at zero stress for a further 300 seconds, and the degree of elongation is measured as a percentage ($\epsilon_{300}$).

The % recovery at 300 seconds ($R_{300}$) is given by the formula below:

$$R_{300} = ((\epsilon_{max} - \epsilon_{300})/\epsilon_{max}) \times 100$$

The compositions according to the invention can comprise, as the at least one crosslinked thickening polymer (B), crosslinked (meth)acrylic acid copolymer, such as the products Carbopol 1342 and 1382, Pemulen TR1 and Pemulen TR2 sold by Goodrich.

The compositions according to the invention in particular can comprise, as the at least one crosslinked thickening polymer (B), at least one crosslinked (meth)acrylic acid homopolymer. In particular, the polymers Carbopol 940, Carbopol 941, Carbopol 980, Carbopol 981, Carbopol ETD 2001, Carbopol ETD 2050, Carbopol 2984, Carbopol 5984 and Carbopol Ultrez 10 sold by Goodrich; Synthalen K, Synthalen L and Synthalen MS sold by 3V; Modarez V1250 PX, Modarez V2000 PX, Viscaron A1600 PE and Viscaron A700 PE sold by the company Protex, can be used as the at least one polymer (B).

In the compositions in accordance with the invention, the at least one film-forming polymer (A) is generally present in an amount ranging from 0.05% to 20% by weight, such as from 0.5% to 10% by weight, and further such as from 1% to 8% by weight, relative to the total weight of the composition.

In the compositions in accordance with the invention, the at least one crosslinked thickening polymer (B) is generally present in an amount ranging from 0.6% to 2% by weight, such as from 0.7% to 1.8% by weight, relative to the total weight of the composition.

The cosmetically acceptable medium can comprise a medium chosen from water, at least one cosmetically acceptable solvent, such as alcohols, and water and at least one cosmetically acceptable solvent, wherein such solvents are chosen from $C_1$–$C_4$ alcohols.

Among these alcohols which may be mentioned are ethanol and isopropanol, and in particular, ethanol.

The compositions of the invention can also comprise at least one additive chosen from thickeners other than those of the invention, surfactants, fragrances, preserving agents, sunscreens, proteins, vitamins, non-fixing polymers, mineral, plant and synthetic oils, provitamins, volatile and non-volatile, linear and cyclic, modified and unmodified silicones and any other additive conventionally used in cosmetic compositions intended to be applied to the hair.

One skilled in the art should take care to select the optional compound(s) to add to the composition according to the invention such that the advantageous properties associated with the composition in accordance with the invention are not, or are not substantially, adversely affected by the addition envisaged.

The compositions in accordance with the invention can be in the form of thickened compositions and in particular in the form of gels.

The compositions in accordance with the invention can be applied to wet or dry hair.

The invention will be illustrated more fully with the aid of the non-limiting example which follows.

All the percentages are relative percentages by weight relative to the total weight of the composition, and a.m. means active material.

| | |
|---|---|
| Hystretch V29 | Acrylic acid/ethyl acrylate/acrylonitrile/acrylamide polymer sold by Hoechst |
| Aristoflex A | Vinyl acetate/crotonic acid copolymer sold by Hoechst |
| Synthalen K | Crosslinked acrylic acid homopolymer sold by 3 V |

COMPARATIVE EXAMPLE

Compositions 1 and 2 below were prepared in the form of gels.

Composition 1 (Invention):

| | |
|---|---|
| Hystretch V29 | 3% a.m. |
| Synthalen K | 1% a.m. |
| AMP | qs neutralization of the Synthalen |
| Preserving agent | qs |
| Water | qsp 100% |

Composition 2: (Comparative)

| | |
|---|---|
| Aristoflex A | 3% a.m. |
| Synthalen K | 1% a.m. |
| AMP | qs neutralization of the Synthalen |
| Preserving agent | qs |
| Water | qsp 100% |

(a) Mechanical Properties of the Film-forming Polymers on the Hair

| | Hystretch V29 (invention) | Aristoflex A (comparative) |
|---|---|---|
| Degree of elongation at break ($\epsilon_r$) in % | 680 | 1500 |
| Instantaneous recovery ($R_i$) in % | 80 | 28 |
| Recovery at 300 seconds ($R_{300}$) in % | 90 | 54 |

(b) Evaluation of the Hold of the Hairstyle on Heads

On 5 models, the hair was divided into two symmetrical sides (left and right). Compositions 1 and 2 were each applied to one side of the head, on shaped dry hair without application of a product beforehand. The application of the products lead to the formation of "bonded locks", i.e., to the formation of small locks of hair adhered together, giving the head of hair a wet look.

The fixing effect was noted immediately after the application. The models returned 5 hours after the application, and the level of fixing of each side of the hair was noted at that time. This is the same as comparing the hold of the bonded locks 5 hours after forming them.

Composition 1: the bonded locks hold together very well

Composition 2: most of the bonded locks have come undone. The hairstyle no longer looks the same as it did immediately after application.

The cosmetic properties of the hair were noted when the models returned 5 hours after application:

| Composition | Disentangling | Softness | Feel |
|---|---|---|---|
| 1 | very easy | soft hair | correct |
| 2 | moderately easy | slightly coarse hair | charged |

Hair treated with composition 1 shows better cosmetic properties than hair treated with composition 2.

(c) Evaluation of the Hold of the Hairstyle on Wigs

The hold performance of compositions 1 and 2 was also determined by monitoring over time the change in "bonded locks" under mechanical stirring.

The supports used were wigs of about 20 g of European chestnut-brown hair 20 cm long.

The compositions were applied to the wigs, the hair of which is washed and shaped, at a rate of 2 g of gel to each wig.

The wigs were left to dry for 1 hour at room temperature.

The wigs were then stirred for one hour by rotary movements under a conditioned atmosphere at 50% relative humidity at 24° C.

The cohesion of the bonded locks after this stirring was noted.

The wig treated with formula 1 had bonded locks that were much more resistant and better shaped after stirring for one hour, than the wig treated with formula 2.

The result of this is that the compositions in accordance with the invention gave better results in terms of hold of the hairstyle over time than the compositions in accordance with composition 2.

The cosmetic properties of the hair on wigs after stirring were noted:

| Composition | Disentangling | Softness | Feel |
|---|---|---|---|
| 1 | very easy | soft hair | correct |
| 2 | moderately easy | slightly coarse hair | charged |

Hair treated with composition 1 according to the invention showed better cosmetic properties than hair treated with composition 2.

What is claimed is:

1. A cosmetic composition comprising, in a cosmetically acceptable medium:
   (1) at least one film-forming polymer, wherein a film, obtained by drying a mixture comprising ethanol or water and said at least one film-forming polymer, at room temperature and at a relative humidity of 50%, has a mechanical profile defined by at least:
      (i) a degree of elongation at break ($\epsilon_r$) of greater than or equal to 300%;
      (ii) a recovery at 300 seconds ($R_{300}$) of greater than or equal to 45%; and
      (iii) if the recovery at 300 seconds ($R_{300}$) is from 45% to 60%, then the elongation at break is less than or equal to 1300%; and
   (2) at least one crosslinked thickening polymer comprising at least one (meth)acrylic acid monomeric residue, wherein said at least one crosslinked thickening polymer is present in the composition in an amount of at least 0.6% by weight, relative to the total weight of the composition.

2. A composition according to claim 1, wherein the at least one crosslinked thickening polymer is a crosslinked (meth)acrylic acid homopolymer.

3. A composition according to claim 1, wherein said at least one crosslinked thickening polymer is a crosslinked (meth)acrylic acid copolymer.

4. A composition according to claim 1, wherein said at least one film-forming polymer is present in an amount ranging from 0.05% to 20% by weight, relative to the total weight of the composition.

5. A composition according to claim 4, wherein said at least one film-forming polymer is present in an amount ranging from 0.5% to 10% by weight, relative to the total weight of the composition.

6. A composition according to claim 5, wherein said at least one film-forming polymer is present in an amount ranging from 1% to 8% by weight, relative to the total weight of the composition.

7. A composition according to claim 1, wherein said at least one crosslinked thickening polymer is present in an amount ranging from 0.6% to 2% by weight, relative to the total weight of the composition.

8. A composition according to claim 7, wherein said at least one crosslinked thickening polymer is present in an amount ranging from 0.7% to 1.8% by weight, relative to the total weight of the composition.

9. A composition according to claim 1, wherein said cosmetically acceptable medium comprises a medium chosen from water, at least one cosmetically acceptable solvent, and water and at least one cosmetically acceptable solvent.

10. A composition according to claim 9, wherein said cosmetically acceptable solvent is chosen from alcohols.

11. A composition according to claim 10, wherein said alcohols are chosen from $C_1$–$C_4$ alcohols.

12. A composition according to claim 11, wherein said $C_1$–$C_4$ alcohols are chosen from ethanol and isopropanol.

13. A composition according to claim 12, wherein said alcohols are ethanol.

14. A composition according to claim 1 further comprising at least one additive chosen from thickeners other than those of the invention, surfactants, fragrances, preserving agents, sunscreens, proteins, vitamins, non-fixing polymers, mineral, plant and synthetic oils, volatile and non-volatile, linear and cyclic, modified and unmodified silicones.

15. A thickened composition comprising, in a cosmetically acceptable medium:
   (1) at least one film-forming polymer, wherein a film, obtained by drying a mixture comprising ethanol or water and said at least one film-forming polymer, at room temperature and at a relative humidity of 50%, has a mechanical profile defined by at least:
      (i) a degree of elongation at break ($\epsilon_r$) of greater than or equal to 300%;
      (ii) a recovery at 300 seconds ($R_{300}$) of greater than or equal to 45%; and
      (iii) if the recovery at 300 seconds ($R_{300}$) is from 45% to 60%, then the elongation at break is less than or equal to 1300%; and
   (2) at least one crosslinked thickening polymer comprising at least one (meth)acrylic acid monomeric residue, wherein said at least one crosslinked thickening polymer is present in the composition in an amount of at least 0.6% by weight, relative to the total weight of the composition.

16. A composition according to claim 15, wherein said thickened composition is a gel.

17. An aerosol device comprising a container comprising:
   (1) at least one film-forming polymer, wherein a film, obtained by drying a mixture comprising ethanol or water and said at least one film-forming polymer, at room temperature and at a relative humidity of 50%, has a mechanical profile defined by at least:
  (i) a degree of elongation at break ($\epsilon_r$) of greater than or equal to 300%;
  (ii) a recovery at 300 seconds ($R_{300}$) of greater than or equal to 45%; and
  (iii) if the recovery at 300 seconds ($R_{300}$) is from 45% to 60%, then the elongation at break is less than or equal to 1300%; and
(2) at least one crosslinked thickening polymer comprising at least one (meth)acrylic acid monomeric residue, wherein said at least one crosslinked thickening polymer is present in the composition in an amount of at least 0.6% by weight, relative to the total weight of the composition.

18. A process for holding or shaping the hairstyle, comprising applying to hair an effective amount of a composition comprising, in a cosmetically acceptable medium:
  (1) at least one film-forming polymer, wherein a film, obtained by drying a mixture comprising ethanol or water and said at least one film-forming polymer, at room temperature and at a relative humidity of 50%, has a mechanical profile defined by at least:
    (i) a degree of elongation at break ($\epsilon_r$) of greater than or equal to 300%;
    (ii) a recovery at 300 seconds ($R_{300}$) of greater than or equal to 45%; and
    (iii) if the recovery at 300 seconds ($R_{300}$) is from 45% to 60%, then the elongation at break is less than or equal to 1300%; and
  (2) at least one crosslinked thickening polymer comprising at least one (meth)acrylic acid monomeric residue, wherein said at least one crosslinked thickening polymer is present in the composition in an amount of at least 0.6% by weight, relative to the total weight of the composition.

19. A process for manufacturing at least one cosmetic product comprising including in said product:
  (1) at least one film-forming polymer, wherein a film, obtained by drying a mixture comprising ethanol or water and said at least one film-forming polymer, at room temperature and at a relative humidity of 50%, has a mechanical profile defined by at least:
    (i) a degree of elongation at break ($\epsilon_r$) of greater than or equal to 300%;
    (ii) a recovery at 300 seconds ($R_{300}$) of greater than or equal to 45%; and
    (iii) if the recovery at 300 seconds ($R_{300}$) is from 45% to 60%, then the elongation at break is less than or equal to 1300%; and
  (2) at least one crosslinked thickening polymer comprising at least one (meth)acrylic acid monomeric residue, wherein said at least one crosslinked thickening polymer is present in the composition in an amount of at least 0.6% by weight, relative to the total weight of the composition.

20. A process according to claim 19, wherein said at least one cosmetic product is a haircare product.

* * * * *

UNITED STATES PATENT AND TRADEMARK OFFICE
CERTIFICATE OF CORRECTION

PATENT NO.    : 6,432,386 B1
DATED         : August 13, 2002
INVENTOR(S)   : Isabelle Rollat-Corvol et al.

It is certified that error appears in the above-identified patent and that said Letters Patent is hereby corrected as shown below:

<u>Title page,</u>
Item [75], Inventors, before "Le Bretonneux" insert -- Montigny --.
Item [57], ABSTRACT,
Line 16, after "monomeric" insert -- residue --.

Signed and Sealed this

Fourth of February, 2003

JAMES E. ROGAN
*Director of the United States Patent and Trademark Office*